United States Patent
Weinstein (10) Patent No.: US 9,060,789 B2
(45) Date of Patent: Jun. 23, 2015

(54) METHOD AND APPARATUS FOR PREPARING AND FUSION OF SMALL JOINTS

(76) Inventor: Robert B. Weinstein, Atlanta, GA (US)

(*) Notice: Subject to any disclaimer, the term of this patent is extended or adjusted under 35 U.S.C. 154(b) by 61 days.

(21) Appl. No.: 13/370,859

(22) Filed: Feb. 10, 2012

(65) Prior Publication Data

US 2012/0209337 A1 Aug. 16, 2012

Related U.S. Application Data (60) Provisional application No. 61/462,938, filed on Feb. 10, 2011.

(51) Int. Cl.
*A61B 17/00* (2006.01)
*A61B 17/16* (2006.01)
*A61B 17/72* (2006.01)

(52) U.S. Cl.
CPC ......... *A61B 17/1682* (2013.01); *A61B 17/1686* (2013.01); *A61B 17/7291* (2013.01)

(58) Field of Classification Search
CPC ........... A61B 17/1664; A61B 17/1666; A61B 17/1668; A61B 17/1682; A61B 17/1684; A61B 17/1686
USPC .................... 606/79–85, 86 R, 87–89, 96–98
See application file for complete search history.

(56) References Cited

U.S. PATENT DOCUMENTS

| | | | |
|---|---|---|---|
| 3,605,527 A * | 9/1971 | Gambale | 76/115 |
| 5,116,165 A * | 5/1992 | Salyer | 407/54 |
| 5,269,786 A | 12/1993 | Morgan | |
| 5,350,383 A | 9/1994 | Schmieding et al. | |
| 5,409,494 A | 4/1995 | Morgan | |
| 5,562,664 A | 10/1996 | Durlacher et al. | |
| 5,562,673 A * | 10/1996 | Koblish et al. | 606/80 |
| 5,573,537 A | 11/1996 | Rogozinski | |
| 6,428,543 B1 | 8/2002 | Salyer | |
| 6,716,234 B2 | 4/2004 | Grafton et al. | |
| 7,029,490 B2 | 4/2006 | Grafton | |
| 7,063,717 B2 | 6/2006 | St. Pierre et al. | |
| 2004/0167519 A1* | 8/2004 | Weiner et al. | 606/60 |
| 2004/0199166 A1* | 10/2004 | Schmieding et al. | 606/79 |
| 2006/0009852 A1* | 1/2006 | Winslow et al. | 623/19.14 |
| 2006/0106393 A1 | 5/2006 | Huebner et al. | |
| 2007/0276396 A1 | 11/2007 | McCarthy | |
| 2008/0086139 A1* | 4/2008 | Bourke et al. | 606/72 |

(Continued)

FOREIGN PATENT DOCUMENTS

EP 1 584 299 A2 12/2005

OTHER PUBLICATIONS

"Coughlin small joint reamer system" to Stryker.*

(Continued)

*Primary Examiner* — David Bates
*Assistant Examiner* — Samuel Hanna
(74) *Attorney, Agent, or Firm* — Trop, Pruner & Hu, P.C.

(57) ABSTRACT

An embodiment includes a system for preparing fusion of joints, such as joints in the toes or fingers of an animal such as a human. The system may include one or more of complementary ball and socket joint reamers. A reamer may be separable from an intramedullary fixation rod. The rod may include channels to prevent rotation of the rod once implanted in bone. Other embodiments are discussed herein.

3 Claims, 5 Drawing Sheets

(56) References Cited

U.S. PATENT DOCUMENTS

2010/0069908 A1    3/2010   Sidebotham et al.
2011/0152868 A1*   6/2011   Kourtis et al. .................. 606/80

OTHER PUBLICATIONS

"Small joint reamer system" to Acumed.*

ARTHREX, "Retroconstruction, Minimally Invasive Options for Anatomic ACL/PCL Reconstruction," 2007, 12 pages.
AOFoundation.org, "Proximal Femur, Reduction and Fixation, Arthoplasty, Chapter 8—Total Hip Replacement," Aug. 12, 2011, 2 pages.
ACUMED, "Create the Perfect Fit Every Time, Small Joint Reamer System," Nov. 2008, 2 pages.

* cited by examiner

FRONT VIEW

Fig. 1

ISOMETRIC VIEW

Fig. 2

TOP VIEW

Fig. 3

BOTTOM VIEW

METHOD AND APPARATUS FOR PREPARING AND FUSION OF SMALL JOINTS

This application claims priority to U.S. Provisional Patent Application No. 61/462,938 filed on Feb. 10, 2011 entitled METHOD AND APPARATUS FOR PREPARING AND FUSION OF SMALL JOINTS.

BACKGROUND

Embodiments of the invention relate to the field of orthopedic surgery where joints (e.g., joints of the fingers and toes) may require surgical fusion. In particular, embodiments of the invention concern a set of devices that can prepare these joints for approximation in a ball-and-socket manner and then secure said joints to achieve fusion.

It is common in the field of orthopedic surgery to perform procedures on the small joints that make up the digits of the hands and feet. Specific disease patterns may affect the joints between phalanges (fingers or toes) causing pain and deformity. These interphalangeal joints, as they are known, can become destroyed from various processes. For example rheumatoid arthritis can cause rapid degeneration of the cartilage on either side of the joint due to repeated and continued inflammatory episodes. Another example is the contraction and subsequent subluxation seen in long standing "hammer toe" deformities, whereby the structures making up the joint permanently adapt to malposition. Once an interphalangeal joint is destroyed, or permanently altered, it is often the case that fusion of the joint is required. Arthrodesis, the fusion of two bones together, involves removing the cartilage or other material between bone ends, and permanently affixing the underlying cancellous bone material of adjacent bones together. This surgical procedure provides the benefit of pain and deformity relief, and prevention of return to the disease (inflammatory or malposition) state.

The optimal result of digital arthrodesis is permanent pain relief and deformity correction. In the course of surgical fusion the joint must be approached, disarticulated, prepared, and affixed. There are common approaches to the digit that are known by those skilled in the art that are essential to avoid neurovascular embarrassment and digit compromise. Generally this includes an incision on the dorsal surface of the affected digit, between the neurovascular bundles and above the tendinous structures. Disarticulation is the process of transection of the tendinous and ligamentous structures that maintain the joint. Sectioning of the collateral ligaments and joint capsule allows the surgeon entry into the joint. Once the joint is disarticulated, the ends of the bones, specifically their cartilaginous surfaces, become evident. It is necessary to then remove the cartilage from the ends of the adjacent bones to expose the underlying vascular or cancellous region. This is done through mechanical means, either by manual instrumentation or high-speed micro-saws. After the cartilage is removed, the bone ends are brought into approximation so the digit is aligned anatomically and affixed through one or more means. Finally, the soft tissue structures of the joint are reassembled. Fusion then occurs as the body forms new vascular channels between the apposed bone over the subsequent six to ten weeks.

Successful fusion of bone ends may depend on three factors: preparation, apposition and stabilization. Any intervening material must be sufficiently removed from the interface between the two bone surfaces without damaging the surface left behind. The ends of the bones may be in direct approximation such that new bone forming cells can bridge the gap. Additionally movement between the bones must be sufficiently below a threshold that delicate blood vessel and ultimately bone tissue formation can occur. This motion restriction may be maintained throughout the period of bone healing. To achieve this result attention must be paid to the manner of joint preparation and apposition.

Micro-surgical saws are high speed instruments designed to cut planar or flat surfaces. The instrument is commonly used in digital arthrodesis since it can rapidly remove the bone ends. There are some drawbacks to use of these machines. For example, excessive heat generation may occur when high speed instrumentation is used, causing bone cell death at the fusion interface. If enough of these cells are compromised the fusion can potentially fail, leading to the development of pseudoarthrosis, or 'nonunion,' as it is known. Additionally, these micro-saws are designed to produce planar (flat) cuts of bone ends. The intent is to then bring these flat surfaces together and have them approximate so that the ends are flush and completely coapted. The user is compelled to create co-planar bone cuts free-hand, since there are no jigs or cutting guides for this type of procedure. It is often difficult to freely make co-planar cuts perfectly such that the bone ends approximate exactly and the digital alignment is anatomic. As a result of imperfect joint apposition, the surgeon must remove additional bone to achieve a flush fit of the bone ends. This may lead to an excessively shortened digit.

Hand instrumentation can be of benefit since the slower process of joint preparation will likely not produce enough heat to cause bone cell death. A rongeur can adequately remove the cartilage from the joint. This instrument consists of two opposing jaws that clamp down on the cartilage and bone, grasping portions and detaching them. Alternatively a surgeon may use a bone nipper, a straight edged forcep designed to cut a planar surface while removing cartilage and bone material. These instruments can be used to remove very small portions of bone so as not to overly shorten a digit.

With repeated use a surgeon may become adept at using these instruments. However the use of hand instrumentation may lead to increased operative times since such procedures require a great deal of dexterity and repetitious movements. Additionally, these types of instruments are designed for multiple uses. However, as with all cutting edges, repeated use can dull the instrument, leading to imperfect cutting surfaces. The user then has to use additional force to remove bone, potentially causing damage to the cells left behind from the crushing effect of a blunt vice across the bone end.

Digital arthrodesis requires fixation to maintain bone approximation throughout the healing process. One example of fixation includes intramedullary stabilization using smooth steel wires, or 'Kirschner wires,' as they are known. These steel wires are introduced from within the arthrodesis site using a variable speed drill and protrude out of the end of the digit after the surgical procedure. They are meant to be removed after several weeks, upon completion of the fusion. They run down the central medullary canal of the bones, maintaining the apposition that the user creates while the bones fuse to one another. The wires stay in position because of friction forces from the bone in which it seats. Being perfectly smooth, often these wires will rotate throughout the healing process. This can create irritation at the skin interface, leading to pain, wire loosening, and possibly infection. Occasionally these wires may be inadvertently disrupted from a pulling force along their axis, such as seen with removing a sock or other dressing. This is because there is no stop measure to prevent axial distraction, such as a locking screw or other mechanism. Additionally, since these wires are perfectly smooth they generally cannot prevent rotation of one bone on another in the several weeks required for fusion.

One other method includes intraosseous loop fixation using fine gauge surgical steel suture. This method provides stability against bone rotation. Since the wires are buried inside the body the problem of inadvertent pulling of the fixation material is alleviated. However the placement of such small loops provides little stability against flexion forces and is often problematic since the procedure is lengthy, requires pre-drilling holes and sturdy bone substance to hold the suture. Consequently this method is less preferred over other methods of fixation.

Yet another method of small bone fixation is seen in devices that achieve bone stability yet are buried inside of the medullary canal of the small bones. These devices are intended to remain implanted permanently. They generally remain in place due to metal relaxation and deformation upon heating (memory-metal alloys), geometric fastening (arrowhead type device), or permanent adjoining (e.g., snap-together.) One skilled in the art of small bone surgery quickly realizes that often there is a need for removal of such devices, such as in cases of infection, inflammation, allergic reactions, malunion, and nonunions. Removal of these devices requires destruction of the surrounding bone to loosen the attachment of the implant. Since these devices cannot be retrieved without significant bone loss it becomes obvious that there is an advantage provided by fixation that is easily removed without additional bone removal.

BRIEF DESCRIPTION OF THE DRAWINGS

Having thus described embodiments of the invention in general terms, reference will now be made to the accompanying drawing, which are not necessarily drawn to scale, and wherein:

DETAILED DESCRIPTION

In the following description, numerous specific details are set forth but embodiments of the invention may be practiced without these specific details. Well-known circuits, structures and techniques have not been shown in detail to avoid obscuring an understanding of this description. "An embodiment", "various embodiments" and the like indicate embodiment(s) so described may include particular features, structures, or characteristics, but not every embodiment necessarily includes the particular features, structures, or characteristics. Some embodiments may have some, all, or none of the features described for other embodiments. "First", "second", "third" and the like describe a common object and indicate different instances of like objects are being referred to. Such adjectives do not imply objects so described must be in a given sequence, either temporally, spatially, in ranking, or in any other manner. "Connected" may indicate elements are in direct physical or electrical contact with each other and "coupled" may indicate elements co-operate or interact with each other, but they may or may not be in direct physical or electrical contact. Also, while similar or same numbers may be used to designate same or similar parts in different figures, doing so does not mean all figures including similar or same numbers constitute a single or same embodiment.

Embodiments of the invention include various methods and systems for small joint preparation that overcome the deficiencies in the prior art. Various embodiments of the invention include, for example: (1) a method of joint preparation that causes minimal trauma to the bone; (2) a method of joint preparation that allows precise amounts of bone to be resected; (3) a method of joint preparation that permits exact approximation of the bone ends, permitting the surgeon anatomic placement of the digit whilst maintaining bone contact; (4) a method of joint preparation that uses predictably sharp instrumentation, such as seen with single use devices; (5) a surgical instrument that can effectively and accurately prepare a joint for fusion while hastening the operative procedure; and (6) a device that can be implanted and used for maintaining stability of small bone ends throughout the healing process and be explanted with ease.

Figure 1:
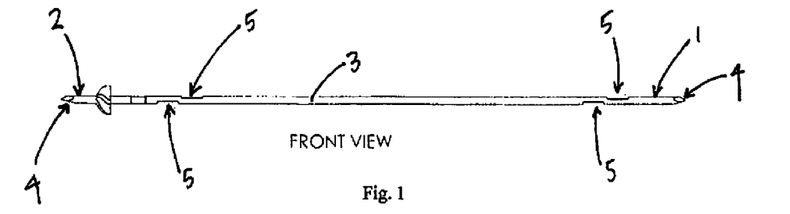
FIG. 1 is a drawing showing a side view of one embodiment of a set of reamers, specifically a double-trocar tipped wire with a dome shaped cutting tool affixed to one end and notches in the smooth wire at specific intervals. The dome tool is preceded by a segment of wire.
Figure 2:
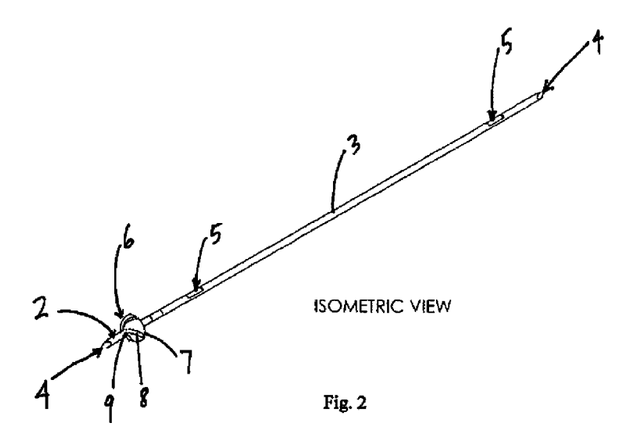
FIG. 2 is a drawing showing an isometric view of the wire of FIG. 1 demonstrating the cutting surface of the dome to be radially disposed along the axis of the wire.
Figure 3:
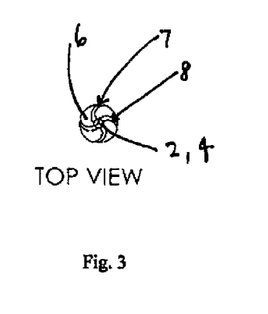
FIG. 3 is a drawing showing one embodiment of the dome cutting surface wherein the cutting flutes are arranged such that upon rotation bone particles will be dispersed to the periphery along new bone to be cut by the flutes.
Figure 4:
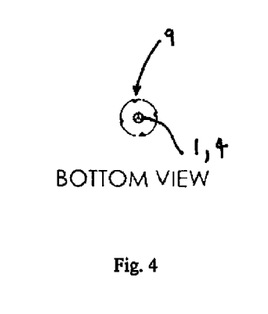
FIG. 4 is a drawing showing the inferior side of the dome surface where the flutes continue to the perimeter allowing bone particles to escape behind the cutting surface.

Referring to an embodiment in FIG. 1, an orthopedic instrument is used to remove tissue from the end of a bone (e.g., toe, finger, and the like) comprising a rotatable body having a proximal end 1, a distal end 2, a longitudinal axis and a longitudinal bore 3 extending from said distal end to said proximal end. The ends of said instrument are sharpened 4. Spaced at intervals along said longitudinal bore are notches 5, alternatively arranged with respect to each other. Referring to FIG. 2, the instrument has a drill tip 6 proximal to said distal end 2 including tip edges 7 positioned around said axis and disposed angularly with a plane normal to said axis for penetrating bone; reaming edges 8 joined to said tip edges and extending longitudinally from said tip edges to said proximal end parallel with said axis for forming a tunnel when said body is rotated in bone, said drill tip being tapered in a distal direction from said reaming edges to said bore; flute surfaces 9 disposed between said tip edges for evacuating bone along said flute surfaces when said body is rotated in bone; and an elongate shank for mounting said body to rotate said body in bone. Evaluation of the geometry of the cutting end of the device reveals that a cup-shaped recess would be produced upon rotation of the cutting end against a bone. FIG. 3 demonstrates the radial appearance of the cutting surface such that when the device rotates particulate matter will be dispersed centrifugally. FIG. 4 demonstrates the inferior portion of the drill tip 6 with flutes 9 extending to the periphery to facilitate bone tissue clearance.

Figure 5:
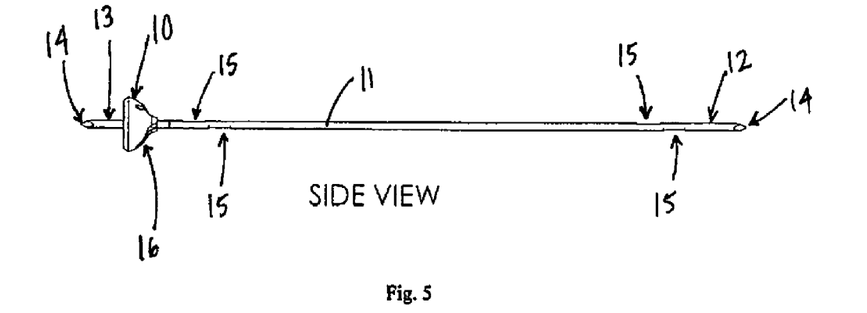
FIG. 5 is a drawing showing a side view of one embodiment of a set of reamers, specifically a double-trocar tipped wire with a cup shaped cutting tool affixed to one end and notches in the smooth wire at specific intervals.
Figure 6:
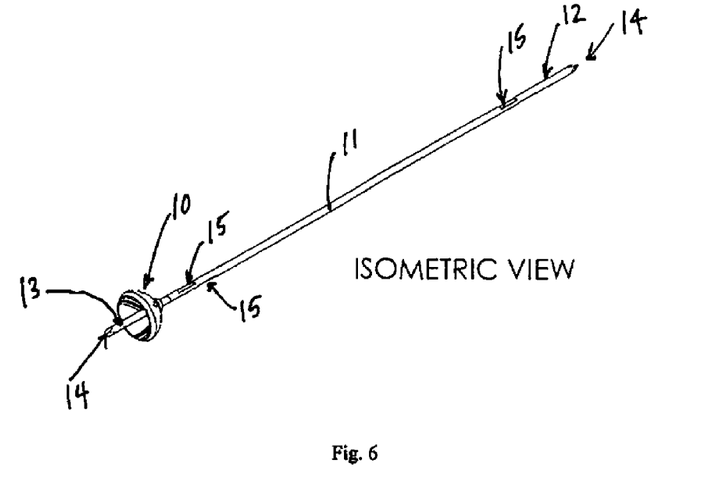
FIG. 6 is a drawing showing an isometric view of the wire of FIG. 5 demonstrating the cutting surface of the cup to be radially disposed along the axis of the wire. The cup is preceded by a segment of wire.
Figure 7:
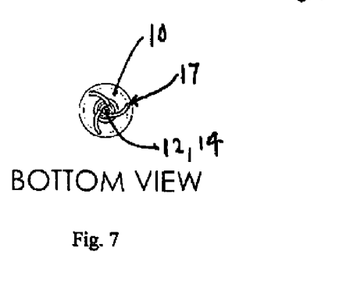
FIG. 7 is a drawing showing the bottom view of the cup cutting surface with open channels for bone to escape during the cutting process.
Figure 8:
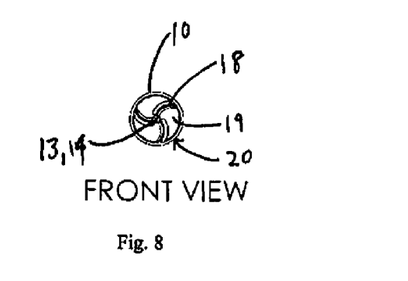
FIG. 8 is a drawing showing the top view of the cup cutting surface with cutting flutes radially disposed of along the internal cup surface.

Referring to FIG. 5, an embodiment includes a similar device to the embodiment in FIG. 1 with a corresponding drill tip 10. This drill tip is affixed to a longitudinal bore 11 with similar or identical dimensions as that of FIG. 1, having a proximal end 12, a distal end 13, sharpened ends 14, and alternatively spaced notches 15. One can appreciate the leading portion of the instrument as it projects forward to the cutting instrument 10. Evaluation of the geometry of the cutting end 10 reveals that a dome-shaped recess would be produced upon rotation of the cutting end against a bone. Said recess would correspond to the cup shaped recess produced by use of the device in FIG. 1. The concavity of said second reamer is of a corresponding radius 16 to the convexly shaped reamed surface, so that when the two bone ends are brought into approximation a ball and socket arrangement is achieved. FIG. 6 shows an isometric view of the embodiment of FIG. 5, demonstrating the cutting surface to be placed proximal to a leading segment of the wire such that said segment assists the user to place the device centrally in the long bone to be cut, and said lead segment projects ahead of the cutting edge of the reaming device. FIG. 7 demonstrates the radial position of the cutting flutes 17 such that bone is delivered to the periphery of the device during use. FIG. 8 depicts the inferior surface of the cutting device of FIG. 5 revealing the open channel portions 18 of said cutting device that allow bone to escape from within the confines of the cutting area 19. The peripheral edge of the cutting device is closed and beveled 20 such that the device defines the closed area 19 in which reaming will occur and can bore into the cutting surface peripherally.

Figure 9:
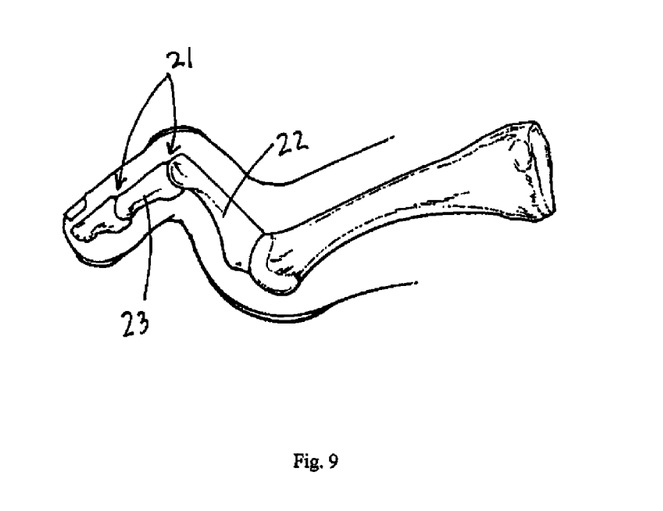
FIG. 9 is a drawing depicting the joints of a toe as they naturally articulate with each other.
Figure 10A:
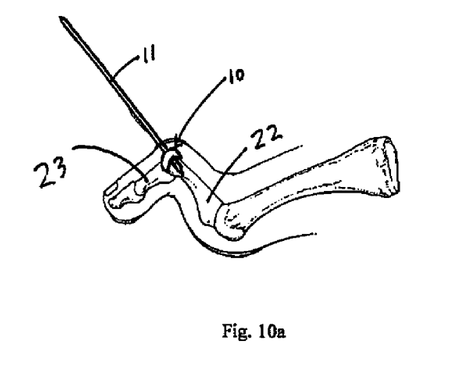
FIGS. 10a and 10b are drawings showing, in one embodiment, a cup reamer placed in contact with one side of a joint, specifically the proximal bone, and the resultant curved surface left behind after cutting.
Figure 10B:
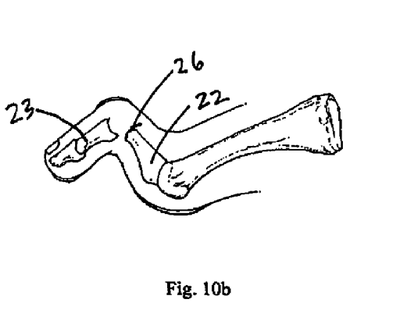
Figure 11A:
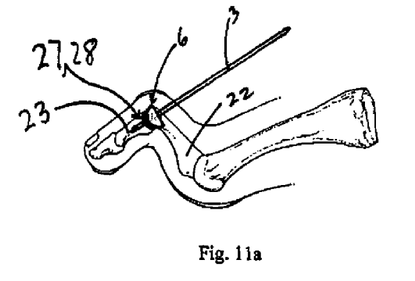
FIGS. 11a and 11b are drawings showing, in one embodiment, a dome reamer placed in contact with one side of a joint, specifically the distal bone, and the resultant curved surface left behind after cutting.
Figure 11B:
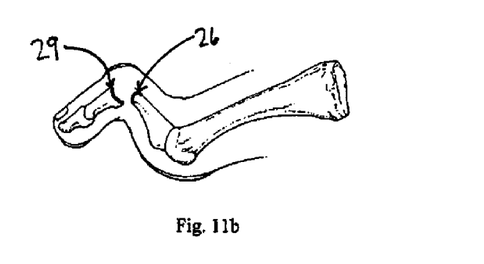
Figures 12, 13:
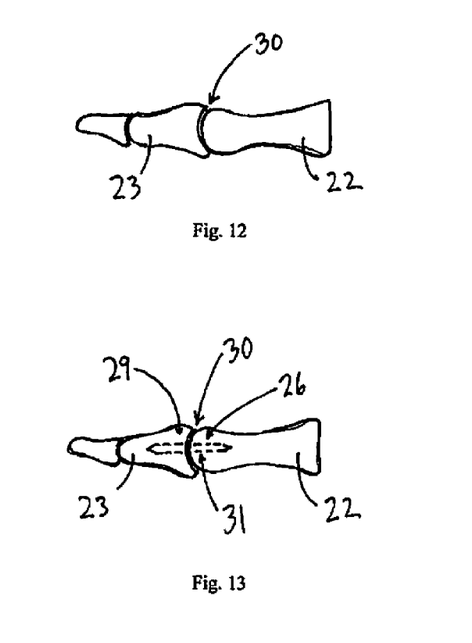
FIG. 12 is a drawing depicting apposition of the bone ends after cutting.
FIG. 13 is a drawing showing the joint surfaces as prepared and pre-drilled for intramedullary fixation.

Referring now to FIG. 9, the normal articulations 21 of the bones in the lesser toes is appreciated from a sagittal plane section. The proximal phalanx 22 articulates with the middle phalanx 23 at the interphalangeal joint 21. In this image we see the pathologic state known as a "hammer toe." FIG. 10a shows engagement 24 of an embodiment of a cup reamer with the head of the proximal phalanx 22 and 10b shows the contoured head 26 of said phalanx after use of the apparatus. FIG. 11a shows engagement 27 of an embodiment of a dome reamer with the base of the middle phalanx 28 and 11b shows the contoured base 29 of said phalanx after use of the apparatus. FIG. 12 demonstrates apposition of the bone ends 30 and one can appreciate the precise geometry of the opposed surfaces generated by use of corresponding cutting devices.

Figures 14A, 14B:
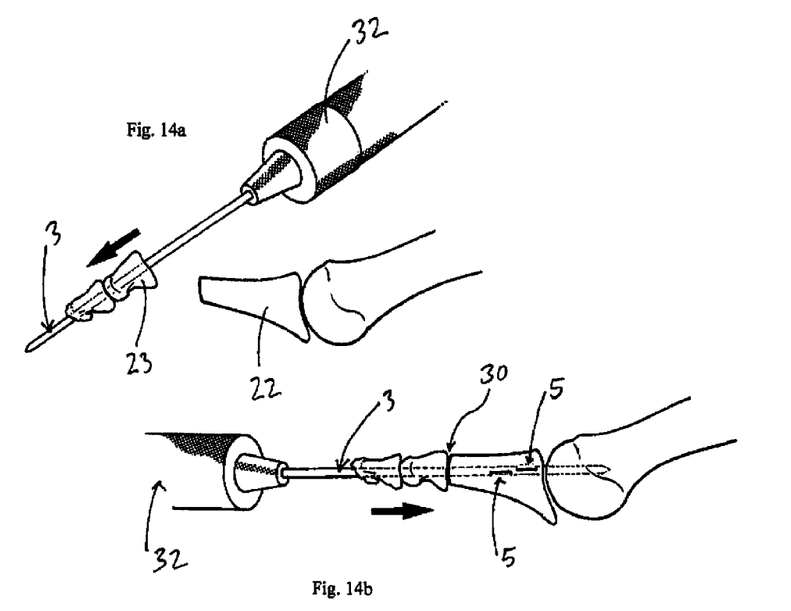
FIGS. 14a and 14b are drawings showing placement of a wire, in one embodiment of the invention, in the predrilled hole and advanced out of the end of the toe to stabilize the joint through the healing phase.

Referring now to FIG. 13, the approximate bone ends 26 and 29 are appreciated to be "pre-drilled" 31 by the leading wire distal tip 13 and 2 respectively. Fixation is then accomplished in the manner depicted in FIGS. 14a and 14b, using the wire of the embodiments of FIG. 1 and FIG. 5 whilst affixed to a driving instrument 32 such as a pneumatic or electrically powered apparatus. The user may remove the cutting portion of the wire (e.g., the domed or cupped reamers) prior to use as intramedullary fixation. One can appreciate the slots 5 along the segment of wire that resist rotation and shifting of the distal bone on the proximal bone during the healing phase.

Figure 15:
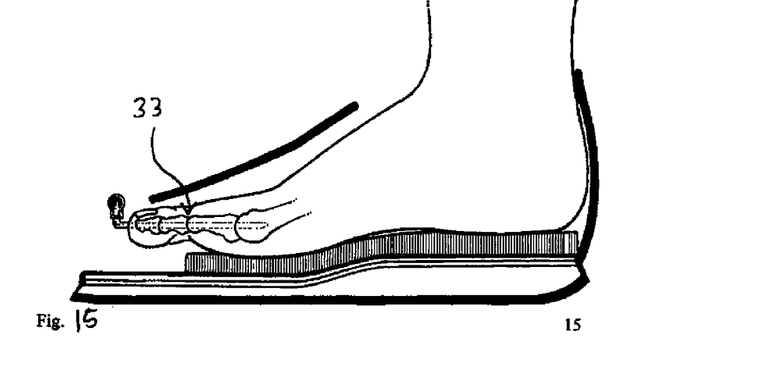
FIG. 15 is a drawing showing a toe in a final fixed position with the intramedullary fixation device.

FIG. 15 demonstrates the final appearance of the prepared and fixated toe joint 33.

In one embodiment, after joint exposure the surgeon prepares the joint for either arthroplasty or arthrodesis. Embodiment of the above reamers are sequentially attached to variable speed drill/wire drivers used to traditionally drive fixation wires along the canals of the bones being affixed. The surgeon begins with a cup reamer (e.g., FIG. 5), which is placed against the end of a bone, such as the head of a proximal phalanx. The driving device is engaged and the reamer tip rotates. The tip of the instrument is brought to the center of the head of the bone to be sectioned. The instrument is advanced forward as the wire secures the cutting device in the bone and defines the center of region to be reamed. Further advancement allows the beveled edge of the cutting device to engage the bone that then defines the closed perimeter and begins the bone material removal. The reaming edges begin cutting and in centrifugal manner bone material is delivered to the periphery and out of the open flutes. The reamer is advanced until the head of the bone is fully prepared. Upon removal of the device the head of the bone will have the shape of a dome with an arc geometry precisely controlled by the cutting surface. The user then performs a similar technique on the adjacent side of the joint using a corresponding reamer having a dome shaped cutting tool (e.g., FIG. 1). Preparation will leave a cup-shaped recess of a geometry corresponding to the arcuate dimension of the dome on the adjacent bone as well as a predrilled hole for placement of fixation.

An embodiment not only prepares the joint for fusion but also fixates the bones during this process. The reaming device is a cutting cone/dome or cup, as the case may be, and serves but one function along the shaft of a metal wire. Proximate to the cutting portion of the wire is a set of grooves or channels in the otherwise smooth wire. These grooves serve to prevent inadvertent distraction or rotation of the bone if the wire is used for intramedullary fixation, since bone will occupy the space against the flattened portion of the wires, adding increased resistance to these disruptive forces.

After joint preparation, the surgeon removes the cutting portion from the rest of the instrument. This can easily be accomplished with a standard wire cutter. The wire is then used in a manner typical of small bone fixation, first advancing out of the end of one bone, then reapproximation of the joint to be fused and retrograde advancement into the other bone.

Embodiments of dome and cup-shaped reamer systems can accomplish several functions. For example, the reamer removes the exact amount of bone that the user desires. The user can remove more or less bone depending on how long the reamer is applied. The reamer removes bone under low or high speed, as the user may appreciate, hastening the operative procedure. Since the reamer creates a dome and corresponding cup shape for fusion the surgeon can then expect complete coaptation of the bone ends upon approximation. The reamer pre-drills for fixation of the bones. The reamer can then simply be modified by removing the cutting surface, rendering the instrument a fixation device as well. Notches along the device help to affix the device within the bone during healing.

The reamers in an embodiment are made of surgical stainless steel or other medical grade material, as the wire will also serve to affix the bones at least temporarily during the healing process.

While embodiments of the invention have been described with respect to a limited number of embodiments, those skilled in the art will appreciate numerous modifications and variations therefrom. It is intended that the appended claims cover all such modifications and variations as fall within the true spirit and scope of this present invention.

What is claimed is:

1. A small joint reaming system for arthrodesis comprising:
a first elongate member;
a first wire (a)(i) including stainless steel, (a)(ii) extending along a first longitudinal axis between a proximal end and a distal end of the first wire, (a)(iii) including a first trocar tip at the distal end of the first wire; (a)(iv) including a first leading segment comprising an elongated rod extending between the first trocar tip and the first elongate member, which has a concave surface facing the first trocar tip, displacing the first trocar tip distally from the first elongate member; (a)(v) including a first trailing segment extending proximally from the first elongate member towards the proximal end of the first wire;
at least one first radial through channel (b)(i) extending through the concave surface, (b)(ii) radially extending from a central portion of the first elongate member at the first longitudinal axis towards a perimeter of the first elongate member, (b)(iii) with at least one cutting edge, raised from the concave surface and extending from the central portion of the first elongate member towards the perimeter of the first elongate member, configured to ream a convex shaped first bone when placed in contact with the first bone and rotated axially about the first longitudinal axis;
wherein (c)(i) the first wire, the first leading segment, the first trailing segment, and the first trocar tip are monolithic with one another; (c)(ii) the first leading segment is configured to center the first elongate member when reaming the first bone; and (c)(iii) rotation of the first wire about the first longitudinal axis causes the first elongate member to rotate about the first longitudinal axis;
wherein the first elongate member includes: (d)(i) a concave cup shape configured to ream a convex surface on the first bone, (d)(ii) a closed perimeter, located at a distal end of the first elongate member, to define a first region to be reamed, and (d)(iii) a non-expandable circular beveled edge that has a diameter unequal to a diameter of the closed perimeter and which is located proximal to the closed perimeter;
a second elongate member;
a second wire (e)(i) including stainless steel, (e)(ii) extending along a second longitudinal axis between a proximal end and a distal end of the second wire, (e)(iii) including a second trocar tip at the distal end of the second wire; (e)(iv) including a second leading segment comprising an elongated rod extending between the second trocar tip and the second elongate member, which has a convex surface facing the second trocar tip, displacing the second trocar tip distally from the second elongate member; (e)(v) including a second trailing segment extending proximally from the second elongate member towards the proximal end of the second wire;
wherein (f)(i) the second wire, the second leading segment, the second trailing segment, and the second trocar tip are monolithic with one another; (f)(ii) the second leading segment is configured to center the second elongate member when reaming a second bone; and (f)(iii) rotation of the second wire about the second longitudinal axis causes the second elongate member to rotate about the second longitudinal axis; and
wherein the second elongate member includes (g)(i) a convex cup shape configured to ream a concave surface on the second bone; and (g)(ii) at least one cutting edge, raised from the convex surface and extending from the central portion of the second elongate member towards the perimeter of the second elongate member, configured to ream the second bone when placed in contact with the second bone and rotated axially about the second longitudinal axis.

2. The system of claim 1, wherein the first leading segment is configured to drill a pilot hole for intramedullary fixation in the bone.

3. The system of claim 1, wherein the closed perimeter is between the first trocar point and a proximal end of the first elongate member.

* * * * *